United States Patent
Mehlberg et al.

(10) Patent No.: US 9,567,272 B2
(45) Date of Patent: Feb. 14, 2017

(54) FCC PROCESS WITH A DEHYDROGENATION ZONE FOR MAX PROPYLENE PRODUCTION

(71) Applicant: UOP LLC, Des Plaines, IL (US)

(72) Inventors: Robert L. Mehlberg, Wheaton, IL (US); Michael R. Smith, Rolling Meadows, IL (US); Trung Pham, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 306 days.

(21) Appl. No.: 14/316,241

(22) Filed: Jun. 26, 2014

(65) Prior Publication Data
US 2015/0376090 A1    Dec. 31, 2015

(51) Int. Cl.
| C07C 5/333 | (2006.01) |
| C07C 2/56 | (2006.01) |
| C07C 2/58 | (2006.01) |
| C07C 7/04 | (2006.01) |
| C10G 11/00 | (2006.01) |

(52) U.S. Cl.
CPC ............ C07C 5/333 (2013.01); C07C 7/04 (2013.01); C10G 11/00 (2013.01)

(58) Field of Classification Search
CPC ..................... C07C 2/56; C07C 2/58
See application file for complete search history.

(56) References Cited

U.S. PATENT DOCUMENTS

| 4,787,967 A | 11/1988 | Herbst |
| 4,871,446 A | 10/1989 | Herbst |
| 4,980,053 A | 12/1990 | Li |
| 4,990,314 A | 2/1991 | Herbst |
| 5,296,131 A | 3/1994 | Raterman |
| 5,965,012 A | 10/1999 | Lomas |
| 6,010,618 A | 1/2000 | Lomas |
| 7,728,185 B2* | 6/2010 | Senetar ............... C07C 4/06 585/259 |
| 2012/0071701 A1* | 3/2012 | Glover ............... C07C 2/56 585/324 |

* cited by examiner

Primary Examiner — In Suk Bullock
Assistant Examiner — Youngsul Jeong

(57) ABSTRACT

A process is presented for the production of light olefins. The process provides for the separation of the effluent stream from a catalytic cracking process into a stream having light olefins and a stream having heavier hydrocarbons. The heavier stream is oligomerized to generate an oligomer stream having heavier hydrocarbons, and then separated into a stream to be passed to the catalytic cracking process, and a stream to be passed to a reforming unit.

15 Claims, 3 Drawing Sheets

FCC PROCESS WITH A DEHYDROGENATION ZONE FOR MAX PROPYLENE PRODUCTION

FIELD OF THE INVENTION

The present invention is in the field of light olefin production. This invention relates to a new process for increasing light olefin yields.

BACKGROUND

Catalytic cracking is the process of breaking larger hydrocarbon molecules into smaller hydrocarbon molecules through contacting the larger hydrocarbon molecules with a catalyst at reaction conditions. The catalytic cracking process is one method used to produce ethylene and propylene from hydrocarbon feedstocks. The ethylene and propylene are important chemicals for the production of the respective plastics polyethylene and polypropylene, two important plastics having a wide variety of uses, such as a material for fabrication of products and as a material for packaging. Other uses of these chemicals include the production of vinyl chloride, ethylene oxide, ethylbenzene and alcohols. Hydrocarbons used as feedstock for light olefin production include natural gas, petroleum liquids, and carbonaceous materials including coal, recycled plastics or any organic material.

Currently, the majority of propylene production is from steam cracking. However, the demand for propylene is growing faster than the ability to increase production of propylene with steam crackers. Fluid catalytic cracking (FCC) provides an alternative method of meeting the demand for the production of propylene.

One process for enhancing propylene yield is disclosed in U.S. Pat. No. 4,980,053, where a deep catalytic cracking process is disclosed. The process requires 5-10 seconds of contact time, and uses a mixture of Y-type zeolite and a pentasil, shape-selective zeolite. However, the process reports relatively high yields of dry gas.

Other patents disclose short catalyst contact times, but do not recognize significant light olefin yields, such as in U.S. Pat. No. 5,965,012 which discloses an FCC process. The process has a catalyst recycle arrangement with a very short contact time of the feed with the catalyst. However, further cracking takes place in a contacting conduit where regenerated and carbonized catalyst contacts the feed, and not in the riser. Another FCC process is disclosed in U.S. Pat. No. 6,010,618 where there is a very short catalyst and feed contact time in the riser, and the cracked product is quickly removed below the outlet of the riser. Other patents, such as U.S. Pat. No. 5,296,131 disclose very short FCC catalyst contact times, but these processes are operated to improve gasoline production rather than production of light olefins.

Other patents, U.S. Pat. Nos. 4,787,967, 4,871,446, and 4,990,314, disclose the use of two component catalysts used in FCC processes. The two component catalyst systems use a large-pore catalyst for cracking large hydrocarbon molecules and a small-pore catalyst for cracking smaller hydrocarbon molecules.

To enhance propylene yields, shape selective additives are used in conjunction with conventional FCC catalysts containing Y-zeolites. The additives all have essentially the same selectivity characteristics. The problem with current catalysts is that selectivity is limited, and the amount of propylene produced is only a function of the amount of additive used in the catalyst mixture. The propylene yield reaches a maximum at a crystalline shape selective zeolite content in the catalyst blend of approximately 10%.

At high levels of additives, the cracking activity is reduced, and this results in lower conversion. To overcome this, the temperature is increased to increase yield, but at the cost of increased coking of the catalyst, and thereby reducing the catalyst life and yields and requiring more frequent regeneration of catalyst, and at an increase in the undesirable yields of dry gas, or methane and ethane.

While much research has gone into trying new catalysts for enhancing propylene production, increasing light olefin production through other means can overcome limitations of catalysts in the cracking process.

SUMMARY

The present invention is a process that increases light olefin yields through the recovery of hydrocarbon streams having 3 to 5 carbon atoms and oligomerizing the hydrocarbons. The oligomerized hydrocarbons are then passed to a cracking unit to increase the yields of ethylene and propylene.

A first embodiment of the invention is a process for producing light olefins, comprising passing a hydrocarbon stream to a cracking unit to generate a first stream comprising olefins; passing the first stream to a first fractionation unit to generate a second stream comprising C3 and lighter components and a third stream comprising C4 and heavier hydrocarbons; passing the second stream to a light olefins recovery unit to generate a light gas stream, an ethylene product stream, a propylene product stream and a propane recycle stream comprising propane; passing the propane recycle stream to a dehydrogenation unit to generate a fourth stream; passing the fourth stream to a depropanizer column to generate a fifth stream comprising C3s, and a sixth stream comprising C4 and heavier hydrocarbons; passing the fifth stream to the light olefins recovery unit; passing the sixth stream to an oligomerization unit to generate a seventh stream; and passing the seventh stream to the cracking unit.

A second embodiment of the invention is a process for producing light olefins, comprising passing a hydrocarbon stream to a cracking unit to generate a first stream comprising olefins; passing the first stream to a first separation unit to generate a second stream comprising C3 and lighter components, a third stream comprising C4 and C5 hydrocarbons, and a fourth stream comprising C6+ hydrocarbons; passing the second stream to a light olefins recovery unit to generate a light gas stream, an ethylene product stream, a propylene product stream and a propane recycle stream comprising propane; passing the propane recycle stream to a dehydrogenation unit; passing the third stream to the dehydrogenation unit to generate a fifth stream comprising olefins; passing the fifth stream to a depropanizer column to generate a sixth stream comprising C3s, and a seventh stream comprising C4 and heavier hydrocarbons; passing the sixth stream to the light olefins recovery unit; passing the seventh stream to an oligomerization unit to generate an eighth stream; and passing the eighth stream to the cracking unit.

A third embodiment of the invention is a process for producing light olefins, comprising passing a hydrocarbon stream to a fluidized catalytic cracking unit to generate a first stream comprising olefins; passing the first stream to a first separation unit to generate a second stream comprising C3 and lighter components, a third stream comprising C4 and C5 hydrocarbons, and a fourth stream comprising C6+ hydrocarbons; passing the second stream to a light olefins recovery unit to generate a light gas stream, an ethylene product stream, a propylene product stream and a propane recycle stream comprising propane; passing the propane recycle stream to a dehydrogenation unit; passing the third stream to an oligomerization unit to generate a oligomerization process stream; passing the oligomerization process stream to a fractionation unit to generate an overhead stream comprising C5 and lighter hydrocarbons, and a bottoms stream comprising C6 and heavier hydrocarbons; passing the overhead stream to the dehydrogenation unit to generate a fifth stream comprising olefins; passing the bottoms stream to the cracking unit; passing the fifth stream to a depropanizer column to generate a sixth stream comprising C3s, and a seventh stream comprising C4 and heavier hydrocarbons; passing the sixth stream to the light olefins recovery unit; passing the seventh stream to an oligomerization unit to generate an eighth stream; and passing the eighth stream to the cracking unit.

Other objects, advantages and applications of the present invention will become apparent to those skilled in the art from the following detailed description and drawings.

DETAILED DESCRIPTION

Demands for olefins, such as propylene, continue to grow. On purpose propylene production using FCC technology needs to increase to keep up with the demands from the market. By integrating a dehydrogenation reactor zone with the first riser, the light saturate components, including propane, butane, and pentane can be selectively dehydrogenated to olefins. The dehydrogenation reactor zone can include a modular CCR (continuous catalyst regeneration) system. The butenes and pentenes can be separated and oligomerized to form an oligomer stream. This oligomer stream can be cracked to form additional propylene. By adding a recycle system around the dehydrogenation zone and the oligomerization unit, increased yields of light olefins can be achieved.

The present invention increases light olefin production by separating heavier hydrocarbons from a cracking reactor, and performing a partial recombination of larger cracked hydrocarbons that are recycled to the cracking reactor, thereby increasing the light olefins. In a preferred operation, the cracking unit is a fluidized catalytic cracking reactor.

Figure 1:
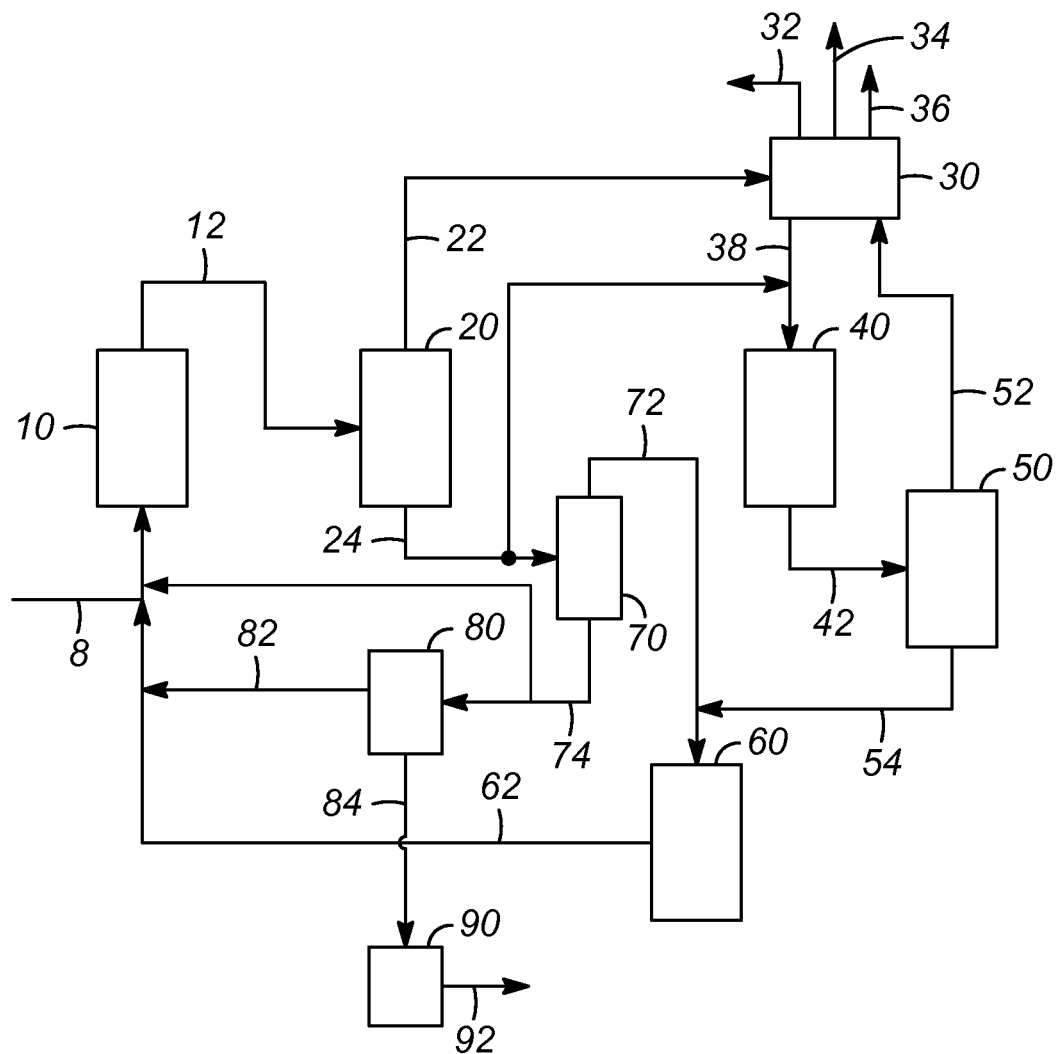
FIG. 1 is a first embodiment of the present invention.

The present invention provides a process for producing light olefins, as shown in FIG. 1. The process includes passing a hydrocarbon stream 8 to a cracking unit 10 to generate a first stream 12 comprising olefins. The first stream 12 is passed to a first fractionation unit 20 to generate a second stream 22 comprising C3 and lighter hydrocarbons and a third stream 24 comprising heavier hydrocarbons. The second stream 22 is passed to a light olefins recovery unit 30 to generate a light gas stream 32, an ethylene stream 34, a propylene stream 36 and a propane stream 38. The propane stream 38 is passed to a dehydrogenation unit 40 to generate a fourth stream 42 comprising olefins. The fourth stream 42 is passed to a depropanizer column 50 to generate a fifth stream 52 comprising propane and propylene, and a sixth stream 54 comprising C4 and heavier hydrocarbons. The fifth stream 52 is passed to the light olefins recovery unit 30. The sixth stream 54 is passed to an oligomerization unit 60 to generate a seventh stream 62 comprising oligomers of C4 and larger hydrocarbons. The seventh stream 62 is passed to the cracking unit 10.

The light olefins recovery unit 30 comprises a plurality of fractionation columns to separate out the individual components of the light olefins process stream 22. Additional equipment can include compressors and heat exchangers and coolers necessary for the separation. This is a well known process and is readily available to one working in the field of fractionation.

The process can further include passing a portion of the third stream 24 to the dehydrogenation unit 40. In an alternative, the third stream 24, or a portion thereof, is passed to a second fractionation unit 70 to generate an eighth stream 72 comprising C4 and C5 hydrocarbons, and a ninth stream 74 comprising C6+ hydrocarbons. The eighth stream 72 can be passed to the oligomerization unit 60.

The ninth stream 74 can comprises aromatics, and aromatics are preferably removed from before recycling heavier hydrocarbons to the cracking unit 10. In cases where the aromatics and naphthene content is sufficiently low, the ninth stream 74 can be passed to the cracking unit 10. When aromatics content is higher, the ninth stream 74 is passed to an aromatics removal unit 80 to generate a tenth stream 82 comprising C6+ alkanes, and an eleventh stream 84 comprising aromatics and naphthenes. In one embodiment, the aromatics removal unit 80 separates the ninth stream 74 into the tenth stream 82 comprising normal alkanes, and the eleventh stream 84 comprising non-normal hydrocarbons. The tenth stream 82 is passed to the cracking unit 10.

The eleventh stream 84 can be passed to a reforming unit 90 to generate an aromatics process stream 92.

The dehydrogenation unit 40 is preferably a modular continuous catalyst regeneration (CCR) unit that can be assembled and added to a petrochemical plant. The process can also be modified to add in stream from other processing units. The other processing units can include, but are not limited to, reformers, hydrocrackers, slurry hydrocrackers, alkylation units, aromatic complexes and natural gas or shale gas condensate recovery units, which can generate process streams comprising alkanes in the C3 to C5 range. These alkanes in the C3 to C5 range are generally of low value, and passing them through this process can upgrade the residual streams to higher value propylene and ethylene.

Figure 2:
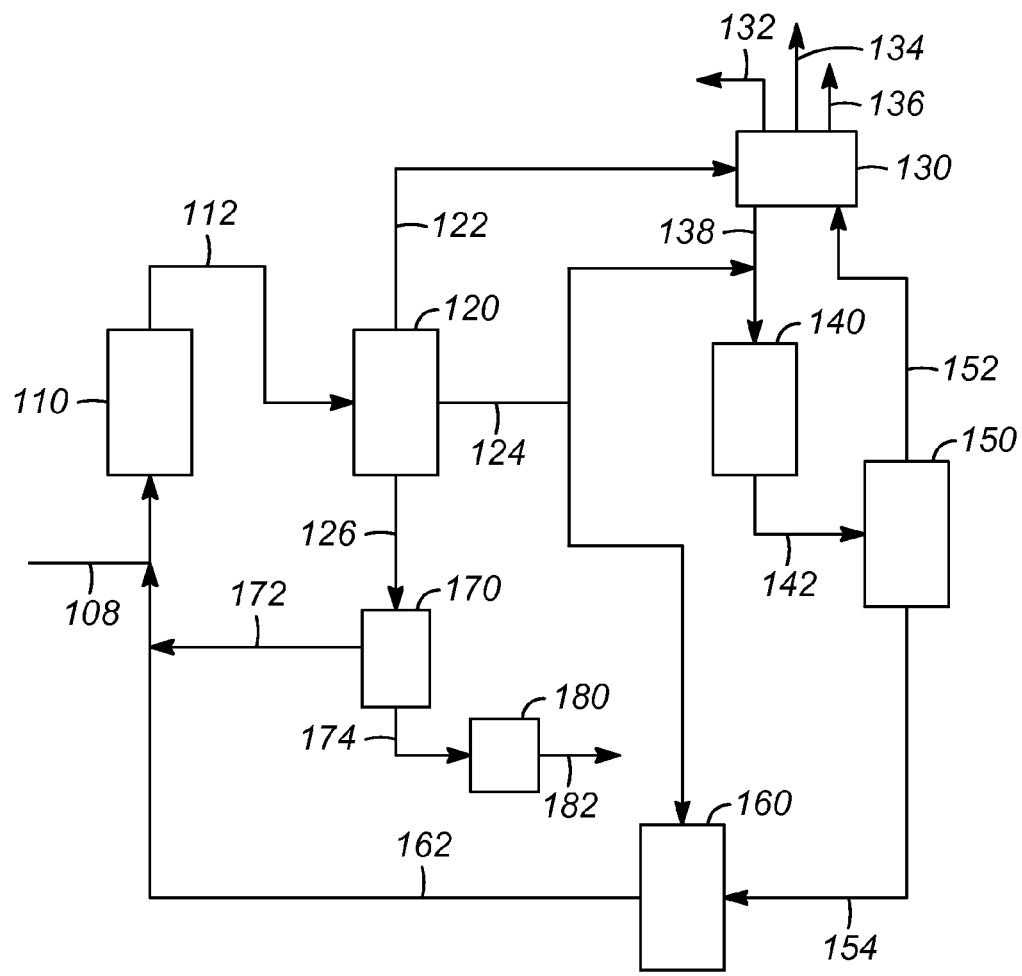
FIG. 2 is a second embodiment of the present invention.

In a second embodiment, as shown in FIG. 2, a process for the production of light olefins is presented. The process includes passing a hydrocarbon stream 108 to a cracking unit 110 to generate a first stream 112 comprising olefins. The first stream 112 is passed to a first fractionation unit 120 to generate a second stream 122 comprising C3 and lighter hydrocarbons and a third stream 124 comprising C4 and C5 hydrocarbons, and a fourth stream 126 comprising C6+ hydrocarbons. The second stream 122 is passed to a light olefins recovery unit 130 to generate a light gas stream 132, an ethylene stream 134, a propylene stream 136 and a propane stream 138 for recycle. The propane stream 138 is passed to a dehydrogenation unit 140 to generate a fifth stream 142 comprising olefins. The fifth stream 142 is passed to a depropanizer column 150 to generate a sixth stream 152 comprising propane and propylene, and a seventh stream 154 comprising C4 and heavier hydrocarbons. The sixth stream 152 is passed to the light olefins recovery unit 130. The seventh stream 154 is passed to an oligomerization unit 160 to generate an eighth stream 162 comprising oligomers of C4 and larger hydrocarbons. The eighth stream 162 is passed to the cracking unit 110. In an alternative, a portion of the third stream 124 is passed to the oligomerization unit 160.

The process can further include passing the fourth stream 126 to a second separation unit 170 to generate a tenth stream 172 comprising C6+ alkanes and an eleventh stream 174 comprising C6+ aromatics and naphthenes. The separation unit 170 can comprise an adsorption separation system for separating out normal or lightly branched alkanes from the fourth stream 126. The tenth stream 172 is passed to the cracking unit 110. It has been found that cracking of normal or lightly branched alkanes is more readily accomplished over other hydrocarbons, and that separating normal alkanes reduces the volume of feed to the cracking unit 110. The process can further include passing the eleventh stream 174 to a reforming unit 180 to generate a process stream rich in aromatics.

Figure 3:
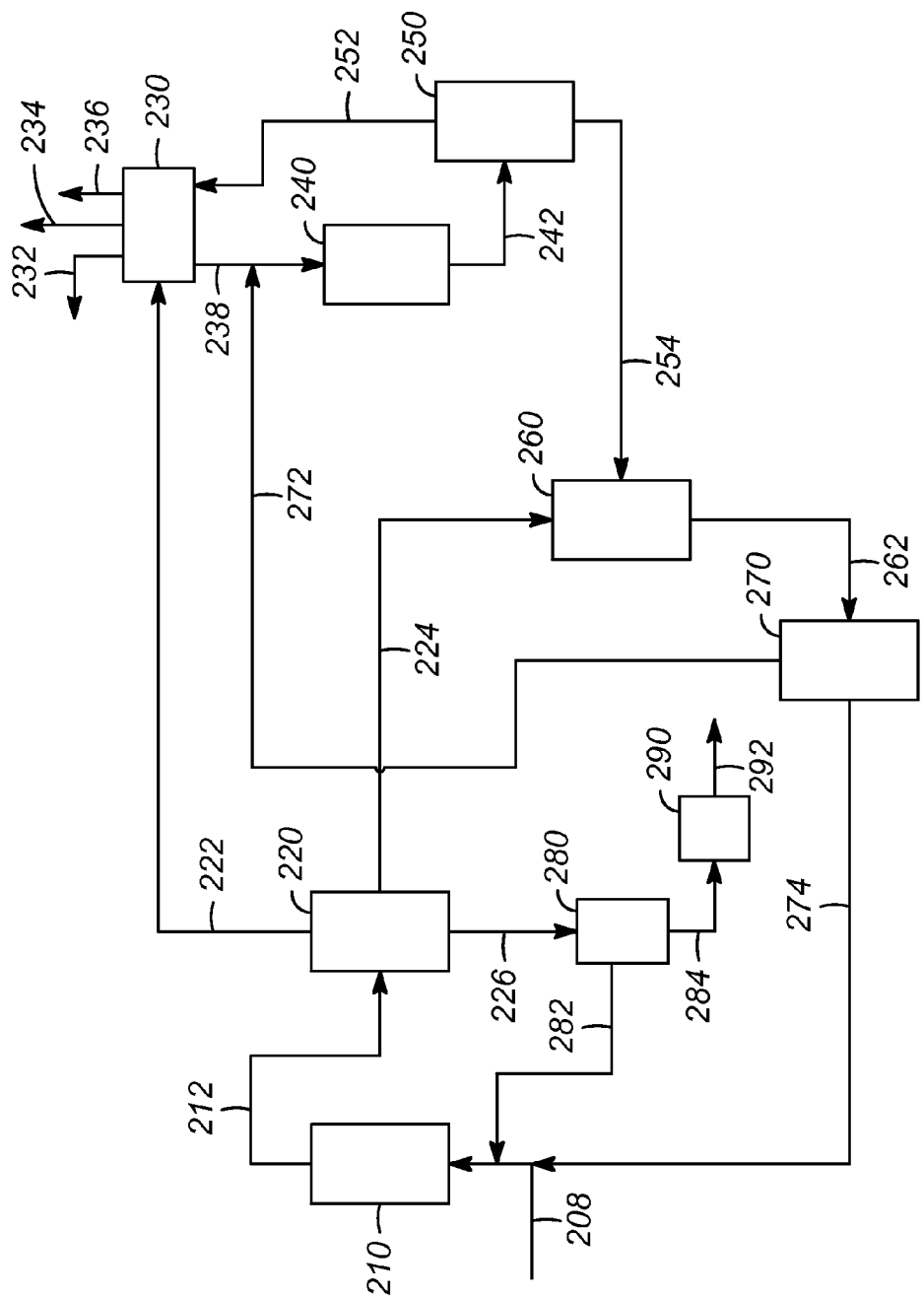
FIG. 3 is a third embodiment of the present invention.

In a third embodiment, the process for the production of light olefins is shown in FIG. 3. The process includes passing a hydrocarbon stream 208 to a cracking unit 210 to generate a first stream 212 comprising olefins. The first stream 212 is passed to a first fractionation unit 220 to generate a second stream 222 comprising C3 and lighter hydrocarbons and a third stream 224 comprising C4 and C5 hydrocarbons, and a fourth stream 226 comprising C6+ hydrocarbons. The second stream 222 is passed to a light olefins recovery unit 230 to generate a light gas stream 232, an ethylene stream 234, a propylene stream 236 and a propane stream 238 for recycle. The propane stream 238 is passed to a dehydrogenation unit 240.

The third stream 224 is passed to an oligomerization unit 260 to generate an oligomerization process stream 262. The oligomerization process stream 262 is passed to a fractionation unit 270 to generate an overhead stream 272 comprising C5 and lighter hydrocarbons, and a bottoms stream 274 comprising C6 and heavier hydrocarbons. The overhead stream 272 is passed to the dehydrogenation unit 240 to generate a fifth stream 242 comprising olefins. The bottoms stream 274 is passed to the cracking unit 210. The fifth stream 242 is passed to a depropanizer column 250 to generate a sixth stream 252 comprising propane and propylene, and a seventh stream 254 comprising C4 and heavier hydrocarbons. The sixth stream 252 is passed to the light olefins recovery unit 230. The seventh stream 254 is passed to the oligomerization unit 260 to generate an eighth stream 262 comprising oligomers of C4 and larger hydrocarbons. The eighth stream 262 is passed to the cracking unit 210 after passing through the fractionation unit 270.

The process can further include passing the fourth stream 226 to a separation unit 280 to generate a tenth stream 282 comprising C6+ alkanes, and an eleventh stream 284 comprising C6+ aromatics and naphthenes. The separation unit 280 can comprise an adsorption separation system to separation the fourth stream 226 into the tenth stream 282 comprising normal alkanes, and the eleventh stream 284 comprising non-normal hydrocarbons. The tenth stream 282 is passed to the cracking unit 210. The process can further include passing the eleventh stream 274 to a reforming unit 290 to generate an aromatics process stream 292 rich in aromatics.

The aromatics process stream 292 can be passed to an aromatics recovery unit, such as a Sulfolane unit for separation and recovery of an aromatics stream, and a raffinate stream comprising non-aromatic hydrocarbons.

Specific Embodiments

While the following is described in conjunction with specific embodiments, it will be understood that this description is intended to illustrate and not limit the scope of the preceding description and the appended claims.

A first embodiment of the invention is a process for producing light olefins, comprising passing a hydrocarbon stream to a cracking unit to generate a first stream comprising olefins; passing the first stream to a first fractionation unit to generate a second stream comprising C3 and lighter components and a third stream comprising C4 and heavier hydrocarbons; passing the second stream to a light olefins recovery unit to generate a light gas stream, an ethylene product stream, a propylene product stream and a propane recycle stream comprising propane; passing the propane recycle stream to a dehydrogenation unit to generate a fourth stream; passing the fourth stream to a depropanizer column to generate a fifth stream comprising C3s, and a sixth stream comprising C4 and heavier hydrocarbons; passing the fifth stream to the light olefins recovery unit; passing the sixth stream to an oligomerization unit to generate a seventh stream; and passing the seventh stream to the cracking unit. An embodiment of the invention is one, any or all of prior embodiments in this paragraph up through the first embodiment in this paragraph wherein the cracking unit is a fluidized catalytic cracking unit. An embodiment of the invention is one, any or all of prior embodiments in this paragraph up through the first embodiment in this paragraph further comprising passing a portion of the third stream to the dehydrogenation unit. An embodiment of the invention is one, any or all of prior embodiments in this paragraph up through the first embodiment in this paragraph further comprising passing the third stream to a second fractionation unit to generate an eighth stream comprising C4 and C5 hydrocarbons, and a ninth stream comprising C6+ hydrocarbons; and passing the eighth stream to the oligomerization unit. An embodiment of the invention is one, any or all of prior embodiments in this paragraph up through the first embodiment in this paragraph further comprising passing the ninth stream to a separation unit to generate a tenth stream comprising C6+ alkanes, and an eleventh stream comprising C6+ aromatics and naphthenes; and passing the tenth stream to the cracking unit. An embodiment of the invention is one, any or all of prior embodiments in this paragraph up through the first embodiment in this paragraph further comprising passing the eleventh stream to a reforming unit to generate an aromatics process stream. An embodiment of the invention is one, any or all of prior embodiments in this paragraph up through the first embodiment in this paragraph wherein the tenth stream comprises normal alkanes, and the eleventh stream comprises non-normal hydrocarbons. An embodiment of the invention is one, any or all of prior embodiments in this paragraph up through the first embodiment in this paragraph wherein the dehydrogenation unit is a modular CCR unit. An embodiment of the invention is one, any or all of prior embodiments in this paragraph up through the first embodiment in this paragraph further comprising passing alkanes in the C3 to C5 range recovered from processing units, that can include but is not limited to, processing units selected from the group consisting of reformers, hydrocrackers, slurry hydrocrackers, alkylation units, aromatic complexes and natural gas or shale gas condensate recovery units.

A second embodiment of the invention is a process for producing light olefins, comprising passing a hydrocarbon stream to a cracking unit to generate a first stream comprising olefins; passing the first stream to a first separation unit to generate a second stream comprising C3 and lighter components, a third stream comprising C4 and C5 hydrocarbons, and a fourth stream comprising C6+ hydrocarbons;

passing the second stream to a light olefins recovery unit to generate a light gas stream, an ethylene product stream, a propylene product stream and a propane recycle stream comprising propane; passing the propane recycle stream to a dehydrogenation unit; passing the third stream to the dehydrogenation unit to generate a fifth stream comprising olefins; passing the fifth stream to a depropanizer column to generate a sixth stream comprising C3s, and a seventh stream comprising C4 and heavier hydrocarbons; passing the sixth stream to the light olefins recovery unit; passing the seventh stream to an oligomerization unit to generate an eighth stream; and passing the eighth stream to the cracking unit. An embodiment of the invention is one, any or all of prior embodiments in this paragraph up through the second embodiment in this paragraph wherein the cracking unit is a fluidized catalytic cracking unit. An embodiment of the invention is one, any or all of prior embodiments in this paragraph up through the second embodiment in this paragraph further comprising passing a portion of the third stream to the oligomerization unit. An embodiment of the invention is one, any or all of prior embodiments in this paragraph up through the second embodiment in this paragraph further comprising passing the fourth stream to a separation unit to generate a tenth stream comprising C6+ alkanes, and an eleventh stream comprising C6+ aromatics and naphthenes; and passing the tenth stream to the cracking unit. An embodiment of the invention is one, any or all of prior embodiments in this paragraph up through the second embodiment in this paragraph further comprising passing the eleventh stream to a reforming unit to generate an aromatics rich process stream. An embodiment of the invention is one, any or all of prior embodiments in this paragraph up through the second embodiment in this paragraph wherein the tenth stream comprises normal alkanes, and the eleventh stream comprises non-normal hydrocarbons. An embodiment of the invention is one, any or all of prior embodiments in this paragraph up through the second embodiment in this paragraph wherein the dehydrogenation unit is a modular CCR unit.

A third embodiment of the invention is a process for producing light olefins, comprising passing a hydrocarbon stream to a fluidized catalytic cracking unit to generate a first stream comprising olefins; passing the first stream to a first separation unit to generate a second stream comprising C3 and lighter components, a third stream comprising C4 and C5 hydrocarbons, and a fourth stream comprising C6+ hydrocarbons; passing the second stream to a light olefins recovery unit to generate a light gas stream, an ethylene product stream, a propylene product stream and a propane recycle stream comprising propane; passing the propane recycle stream to a dehydrogenation unit; passing the third stream to an oligomerization unit to generate a oligomerization process stream; passing the oligomerization process stream to a fractionation unit to generate an overhead stream comprising C5 and lighter hydrocarbons, and a bottoms stream comprising C6 and heavier hydrocarbons; passing the overhead stream to the dehydrogenation unit to generate a fifth stream comprising olefins; passing the bottoms stream to the cracking unit; passing the fifth stream to a depropanizer column to generate a sixth stream comprising C3s, and a seventh stream comprising C4 and heavier hydrocarbons; passing the sixth stream to the light olefins recovery unit; passing the seventh stream to an oligomerization unit to generate an eighth stream; and passing the eighth stream to the cracking unit. An embodiment of the invention is one, any or all of prior embodiments in this paragraph up through the third embodiment in this paragraph further comprising passing the fourth stream to a separation unit to generate a tenth stream comprising C6+ alkanes, and an eleventh stream comprising C6+ aromatics and naphthenes; and passing the tenth stream to the cracking unit. An embodiment of the invention is one, any or all of prior embodiments in this paragraph up through the third embodiment in this paragraph further comprising passing the eleventh stream to a reforming unit to generate an aromatics rich process stream. An embodiment of the invention is one, any or all of prior embodiments in this paragraph up through the third embodiment in this paragraph wherein the tenth stream comprises normal alkanes, and the eleventh stream comprises non-normal hydrocarbons.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for producing light olefins, comprising:
    passing a hydrocarbon stream to a cracking unit to generate a first stream comprising olefins;
    passing the first stream to a first fractionation unit to generate a second stream comprising C3 hydrocarbons and lighter components and a third stream comprising C4 and heavier hydrocarbons;
    passing the second stream to a light olefins recovery unit to generate a light gas stream, an ethylene product stream, a propylene product stream and a propane recycle stream comprising propane;
    passing the propane recycle stream to a dehydrogenation unit to generate a fourth stream;
    passing the fourth stream to a depropanizer column to generate a fifth stream comprising C3 hydrocarbons, and a sixth stream comprising C4 and heavier hydrocarbons;
    passing the fifth stream to the light olefins recovery unit;
    passing the sixth stream to an oligomerization unit to generate a seventh stream;
    passing the seventh stream to the cracking unit;
    passing the third stream to a second fractionation unit to generate an eighth stream comprising C4 and C5 hydrocarbons, and a ninth stream comprising C6+ hydrocarbons;
    passing the eighth stream to the oligomerization unit;
    passing the ninth stream to a separation unit to generate a tenth stream comprising C6+ alkanes, and an eleventh stream comprising C6+ aromatics and naphthenes; and
    passing the tenth stream to the cracking unit.

2. The process of claim 1 wherein the cracking unit is a fluidized catalytic cracking unit.

3. The process of claim 1 further comprising:
    passing a portion of the third stream to the dehydrogenation unit.

4. The process of claim 1 further comprising passing the eleventh stream to a reforming unit to generate an aromatics process stream.

5. The process of claim 1 wherein the tenth stream comprises normal alkanes, and the eleventh stream comprises non-normal hydrocarbons.

6. The process of claim 1 wherein the dehydrogenation unit comprises a continuous catalyst regeneration unit.

7. The process of claim 1 wherein the hydrocarbon stream comprises alkanes in the C3 to C5 range recovered from processing units selected from the group consisting of reformers, hydrocrackers, slurry hydrocrackers, alkylation units, aromatic complexes and natural gas or shale gas condensate recovery units.

8. A process for producing light olefins, comprising:
 passing a hydrocarbon stream to a cracking unit to generate a first stream comprising olefins;
 passing the first stream to a first separation unit to generate a second stream comprising C3 hydrocarbons and lighter components, a third stream comprising C4 and C5 hydrocarbons, and a fourth stream comprising C6+ hydrocarbons;
 passing the second stream to a light olefins recovery unit to generate a light gas stream, an ethylene product stream, a propylene product stream and a propane recycle stream comprising propane;
 passing the propane recycle stream to a dehydrogenation unit;
 passing the third stream to the dehydrogenation unit to generate a fifth stream comprising olefins;
 passing the fifth stream to a depropanizer column to generate a sixth stream comprising C3 hydrocarbons, and a seventh stream comprising C4 and heavier hydrocarbons;
 passing the sixth stream to the light olefins recovery unit;
 passing the seventh stream to an oligomerization unit to generate an eighth stream;
 passing the eighth stream to the cracking unit;
 passing a portion of the third stream to the oligomerization unit;
 passing the fourth stream to a separation unit to generate a tenth stream comprising C6+ alkanes, and an eleventh stream comprising C6+ aromatics and naphthenes; and
 passing the tenth stream to the cracking unit.

9. The process of claim 8 wherein the cracking unit is a fluidized catalytic cracking unit.

10. The process of claim 8 further comprising passing the eleventh stream to a reforming unit to generate an aromatics rich process stream.

11. The process of claim 8 wherein the tenth stream comprises normal alkanes, and the eleventh stream comprises non-normal hydrocarbons.

12. The process of claim 8 wherein the dehydrogenation unit comprises a continuous catalyst regeneration unit.

13. A process for producing light olefins, comprising:
 passing a hydrocarbon stream to a fluidized catalytic cracking unit to generate a first stream comprising olefins;
 passing the first stream to a first separation unit to generate a second stream comprising C3 hydrocarbons and lighter components, a third stream comprising C4 and C5 hydrocarbons, and a fourth stream comprising C6+ hydrocarbons;
 passing the second stream to a light olefins recovery unit to generate a light gas stream, an ethylene product stream, a propylene product stream and a propane recycle stream comprising propane;
 passing the propane recycle stream to a dehydrogenation unit;
 passing the third stream to an oligomerization unit to generate a oligomerization process stream;
 passing the oligomerization process stream to a fractionation unit to generate an overhead stream comprising C5 and lighter hydrocarbons, and a bottoms stream comprising C6 and heavier hydrocarbons;
 passing the overhead stream to the dehydrogenation unit to generate a fifth stream comprising olefins;
 passing the bottoms stream to the cracking unit;
 passing the fifth stream to a depropanizer column to generate a sixth stream comprising C3 hydrocarbons, and a seventh stream comprising C4 and heavier hydrocarbons;
 passing the sixth stream to the light olefins recovery unit;
 passing the seventh stream to an oligomerization unit to generate an eighth stream;
 passing the eighth stream to the cracking unit;
 passing the fourth stream to a separation unit to generate a tenth stream comprising C6+ alkanes, and an eleventh stream comprising C6+ aromatics and naphthenes; and
 passing the tenth stream to the cracking unit.

14. The process of claim 13 further comprising passing the eleventh stream to a reforming unit to generate an aromatics rich process stream.

15. The process of claim 13 wherein the tenth stream comprises normal alkanes, and the eleventh stream comprises non-normal hydrocarbons.

* * * * *